United States Patent [19]

Mach et al.

[11] Patent Number: 5,554,596

[45] Date of Patent: Sep. 10, 1996

[54] VIRUS INHIBITING COMPOSITION

[76] Inventors: Walter Mach, deceased, late of Kirchseon; by Chantal Mach, executor, Wasserburgerstr. 17, D-8011 Kirchseon, both of Germany

[21] Appl. No.: 969,208

[22] Filed: Jan. 27, 1993

Related U.S. Application Data

[63] Continuation of PCT/DE91/00450, May 27, 1991.

[30] Foreign Application Priority Data

May 27, 1990 [DE] Germany ............................ 40 17 091

[51] Int. Cl.$^6$ ............................ A61K 31/70; C07G 1/00; C08L 97/00
[52] U.S. Cl. ............................ 514/22; 424/195.1; 514/54; 530/500; 530/501; 530/502; 530/506; 536/1.11; 536/121; 536/124; 536/123.1
[58] Field of Search ............................ 530/500, 501, 530/502, 506; 424/180, 195.1; 536/1, 121, 124; 514/54, 22

[56] References Cited

U.S. PATENT DOCUMENTS

| | | | |
|---|---|---|---|
| 4,487,766 | 12/1984 | Mach | 514/22 |
| 4,918,059 | 4/1990 | Seubert et al. | 514/33 |
| 4,935,239 | 6/1990 | Machida et al. | 424/195.1 |
| 4,985,249 | 1/1991 | Sakagami et al. | 424/195.1 |
| 5,223,258 | 6/1993 | Machida et al. | 424/405 |

FOREIGN PATENT DOCUMENTS

| | | |
|---|---|---|
| 0035586 | 9/1981 | European Pat. Off. . |
| 0437346 | 9/1991 | European Pat. Off. . |

OTHER PUBLICATIONS

Greene, Warner. *Scientific American*, pp. 99–105, (Sep. 1993). Reference to Guiseppe Pantale & Anthony A. Fauci→p. 102.

Laurence, Jeffrey *Aids Research and Human Retroviruses*, vol. 10 No. 12, pp. 1585–1589, (1994).

Fukuchi et al., *Anticancer Res*, vol. 9(2), pp. 313–317, (1989).

Derwent WPI English abstract, accession No. 91–012374 [02], of Japanese patent publication 2 286 623 of Nov. 26, 1990, based on Japanese application 89 0 108 116 of Apr. 27, 1989, entitled "Anti–Viral Substance", assigned Noda Syokukin Kogyo.

Nicholas Hahon et al./U.S Public Health Service, Morgantown WV "Effects of Lignite Fly Ash Particulates and Soluble Components on the Interferon System," in journal *Environmental Research*, vol. 32, No. 2, pp. 329–343, pub. Dec. 1983 by Academic Press.

*Primary Examiner*—Douglas W. Robinson
*Assistant Examiner*—Howard C. Lee
*Attorney, Agent, or Firm*—Frishauf, Holtz, Goodman, Langer & Chick, P.C.

[57] ABSTRACT

A composite molecular active substance group for use in restitutive chemotherapy against viral infections, which is produced by the process comprising: (a) preparing lignin units by carrying out an extraction in an aqueous media under weakly acidic or alkaline conditions of wood or wood-like materials and/or plant-cell cultures and separating-off the resultant insoluble solids; (b) preparing lignoid units by carrying out an aqueous alkaline extraction at a pH of 7 to 14 of starting materials selected from the group consisting of wood-incarbonization products and bioconverted wood-like materials and separating-off the resultant alkali-insoluble solids; and (c) preparing a water-soluble mixed polymer by reacting the lignin units from step (a) with the lignoid units from step (b), under aqueous alkaline isolating by ultrafiltration a low molecular weight fraction having a molecular weight of no more than 3000 daltons of the mixed polymer, taking a cut between 15 to 40 kilodaltons and discarding the resultant residue, and treating the resultant solution with an H$^+$ cation exchanger at a pH of 3 to 7 and then carrying out further processing.

29 Claims, 9 Drawing Sheets

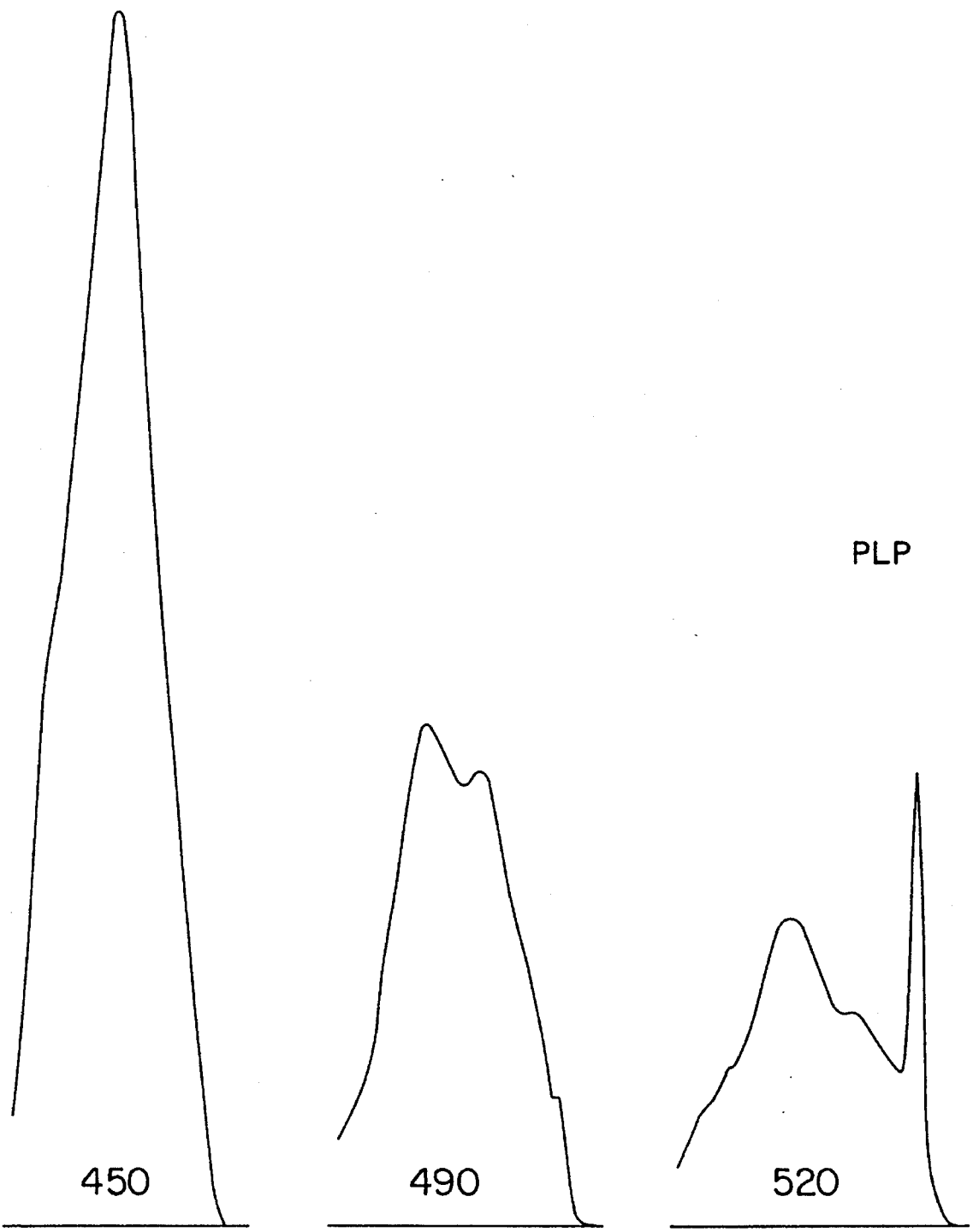

520

520

1) SURVIVAL WITHOUT EXPOSURE AFTER 24 HOURS
2) AFTER EXPOSURE WITHOUT ACTIVE SUBSTANCE
3) AFTER EXPOSURE AND AFTER ADDITION OF 1 µg/ml ACTIVE SUBSTANCE
4) AFTER EXPOSURE AND AFTER ADDITION OF 0.1 µg/ml ACTIVE SUBSTANCE
5) AFTER EXPOSURE AND AFTER ADDITION OF 0.01 µg/ml ACTIVE SUBSTANCE

VIRUS INHIBITING COMPOSITION

This application is a continuation of International Application PCT/DE91/00450 of Dr. Walter MACH, filed May 27, 1991, claiming priority of German application P 40 17 091, May 27, 1990, and designating the United States, in which a Demand for International Preliminary Examination was timely filed, and which has not entered the U.S. national phase.

FIELD OF THE INVENTION

The invention concerns an active substance group for "restitutive chemotherapy" against viral infections and its application.

BACKGROUND

The problem of the combating virus infections has not yet been completely solved. One of the unsolved problems is the relatively rapid mutation of viruses which totally or partly prevents the effect of antiviral drugs or the body's own antibodies. One method to produce resistance against the most diverse types of multiviral infections is to use an "active substance cocktail" with which it is likely that one of the active substances will be efficacious. This principle has been put into practice by the SANDOZ company as the gamma-gobulin preparation, Sandoglobulin. This is a mixture of antibodies from the blood of more than 2000 Central European donors which exhibits a large portion of the spectrum of antibodies against diseases found in the Central European region. This product is therefore presumed to be effective against the most varied of infections because of its large number of different types of antibodies.

Previous attempts at combating virus infections have involved acting on different points in the virus replication process. For example, there are medicaments of the azidothymidine (AZT) type which inhibit reverse transcription by breaking chains. Unfortunately these medicaments lead to considerable side effects in patients.

International studies with dextran sulphate (compounds of saccharide and sulphur with approx. 10 kD) from plant hemicelluloses have shown that this group of substances represents no practical progress for the treatment of HIV patients.

Oral medication with dextran sulphate is problematic among other things because the dextran routes in the bloodstream and its concentration at the site of contract with the virus are not very effective. It also possesses very serious side effects (neuropenia, diarrhea). Clinically as well, no impressive effects could be established.

Attempts have already been made to use genetic engineering to produce isolated CD4 receptor proteins which would bind firmly on the gp 120 virus and therefore neutralize and inactivate it by means of saturation. In order to use this artificial CD4 as a therapeutic agent, however, it would be necessary to inject the artificial protein in high doses. The artificially high excess concentration of a cell sensor which is normally found outside of the membrane of healthy cells represents a multifaceted source of irritation for an organism whose immunological and other reactions cannot be ignored. Soluble CD4 could also bind at the MHC-II glycoproteins and impair their normal function. This could, for example, further increase the seriousness of the immunological deficiency in AIDS patients. In addition, soluble CD4 would have to be repeatedly administered parenterally with a high dosage (Spektrum der Wissenschafi—Dec. 88, p. 116).

One solution to this problem which has been suggested is to produce small sections of the CD4 protein fragments which would be structured in such a way that they would still be recognized by gp 120. If this was successful, the question would still remain of whether this protein fragment might not lead in vivo to immunological counter-regulation and elicit presently unknown disorders in the very lablie AIDS patient.

In 1990, M. LANGE (USA, also see Ärztliche Praxis 15, p. 28 if., Werk-Verlag, D-8032 Gräfelfing) made it clear that with AIDS and ARC patients, the way to the point of no return is by no means a question of the virus production. Presumably HIV acts as an antigen and starts immunological pathomechanisms in motion which tend to escalate. Similarities with autoimmune diseases (e.g. lupus erythematosus) indicate that it cannot be sufficient only to administer anti-HIV chemotherapy. Rather it seems indispensable to include a provision for this development of autoimmunological independence (perpetuation) in the therapy and therefore to design and develop a new form of "anti-escalatory chemotherapy".

According to LANGE, extreme complementary activation occurs in the context of an HIV infection; the anaphylaxis factor C5 a induces the production of tumor necrosis factor and interleukin 1. HIV can cause this cascade to escalate. This has been proven by several groups of researchers. It follows from this finding that a promising anti-HIV chemotherapy must not be restricted solely to HIV inhibition. Rather it must also at least partially interrupt these kinds of autoimmunological by vicious circle mechanisms.

The individual escalatory interaction of the diverse noxae (HIV, causes of opportunistic infections, autoimmune cascades, etc.) must be better understood before a truly curative "chemotherapy" is possible. Only in this way can new treatment approaches be developed.

The success statistics of the current treatments (e.g. mean life expectancy after infection of 13–18 months, 5-year survival rate of 3.4% (San Francisco 1981–87, 4000 patients, published in the J. Amer. Med. Assoc. 263 (1990), 402), indicate that the present purely chemotherapeutically-oriented methods are not satisfactory.

W. J. Mach, the inventor, already demonstrated together with WITTICH and STUHLFAUTH in 1961 that small quantities (parenteral) of the natural pigments of the neopenichromine type described by MACH act as "endogenous control substances" in human beings and, for example, increase the activity of the adrenal cortex.

This is presumably the first indication that redox pigments with quinoid units might be able to stimulate human "anti-escalatory" mechanisms without being itself a protein or hormone and without doing so by means of a nonspecific stimulation effect.

Therefore a future HIV chemotherapy must also (from the immunological perspective) contain anti-escalatory elements to inhibit development towards "the point of no return".

The aim of the invention is to find an active substance, if possible one which can also be administered parenterally, which can achieve a neutralization of the virus without cytotoxicological effects and without eliciting undesirable immunological reactions in the treated patient.

Another aim of the invention is to find an active substance which might also be active against changed/mutated virus forms.

SUMMARY OF THE INVENTION

The invention solves these problems by means of an active substance group for use in restitutive chemotherapy against viral infections. The system is obtained as follows:

(I) Preparation of lignin units high in polysaccharides (PLP) by:

Extraction in aqueous media, under weakly acid to alkaline conditions, from wood or wood-like materials and/or from plant-cell cultures (A); separating off the insoluble solids;

(II) Preparation of low-molecular-weight lignoid units low in polysaccharides (LPL) by:

Aqueous alkaline extraction (pH 7–14) from wood incarbonization products or bioconverted wood-like materials (B); separating off the alkali-insoluble solids:

(Ill) Preparation of a water-soluble reaction product LD(PLP=LPL) with low molecular weight by:

Reacting the product of step I, the lignin units high in polysaccharides (PLP), with the products of step II, the lignoid units low in polysaccharides (LPL), under aqueous alkaline conditions (pH 9–12); isolating the LD fractions of this HD(PLP=LPL) reaction product by ultrafiltration, taking the cut between the nominal values of about 15 to 40 kD, and discarding the residue;

treating the solution with $H^+$ cation exchanger under pH 3 to 7.0, and processing the acid LD(LPL=PLP) system.

If preferred, in step (I) one can also prepare lignin units high in polysaccharides HD(PLP) with less than 100 kD by: Setting the pH value between neutral and weakly acid after the extraction in aqueous media and separating off of insoluble solids; a molecular filtration, preferably ultrafiltration with a suitable cut of less than 100 kD, preferably less than 70 kD, is carried out and the residue is discarded. The solution obtained in this way is processed in step III.

In one preferred form of the invention, low-molecular-weight lignoid units low in polysaccharides LD(LPL) are prepared in step II with less than about 40 kD as follows: After the aqueous alkaline extraction and separating off of alkaline-insoluble solids, an alkaline fragmentation with pH values over 8; molecular separation by ultrafiltration with nominal cut of 15 to 35 kD follows and the product obtained in this way is processed in step III.

It can be advantageous after reacting the high polysaccharide with the low polysaccharide fractions (i.e. the intermediates of step I and step II) to carry out a separation of the solids and then to process the remaining solution further.

The further processing of the acid LD(LPL-PLP) solution obtained from step III can be carried out by means of particle filtering, pyrogen removal by filtering, and then sterilization and if required, manufacturing.

It is advantageous to select the wood-like materials used for extraction in step I from the group consisting of the following:

A1: Native wood like, for example, tree heartwood in the form of "milled wood", softwood, hardwood, PLP systems as they occur, for example, in pomaceous fruit skin or nutshells, general woody plant constituents, preferably as deresinated initial products; grasses like esparto, etc.

A2: Wood analogues like woody substances biotechnologically produced by the preparation (growing) of plant-cell cultures.

A3: Synthetic wood analogues via the production of FREUDENBERG dehydration polymers (DHP) from mono- and/or dilignoles and grafting the DHP's on polysaccharides.

A4: Lignin-polysaccharide complexes (networks) obtained by alkaline extraction from chlorite wood cellulose; as well as mixtures (A1, A2, A3, A4) of these.

Preferably, the initial plant-derived materials used in step II are selected from the group consisting of:

B1: Native products of incarbonization.

B2: Wood bioconverted by lignolytically active microorganisms like white wood-putrefying fungi.

B3: Wood bioconverted through the effect of isolated lignolytic enzymes (like phenoloxidase); or mixtures (B1, B2, B3) of these.

It is advantageous if KOH, NaOH, LiOH, and ammonia are used as bases. However other bases can also be used.

In one typical form of the invention, the lignin units high in polysaccharides (PLP) occur in a concentration of 0.05–10% by weight; preferably up to about 2% by weight and most preferably at about 0.1% by weight.

For example, the product of step I, PLP, is extracted under a pH value of approx. 12–14, preferably in KOH over 1–10 days at room temperature (20° C.), and the extraction is carried out like the PLP extraction under increased temperature up to 120° C., with processing at temperatures of over approx. 100° C. being carried out in the autoclave.

It can also be preferable that the wood incarbonization products are selected from the group consisting of lignites, colored coals, brown coal.

The alkaline extraction with 0.1–0.8M KOH occurs in one preferred form with 0.4M KOH at room temperature. For example, the alkaline fragmentation can be carried out over 7 to 10 days at pH 11 (KOH) at room temperature.

The conversion in step III to the active substance group can occur, for example, at a temperature between room temperature and 120° C. and under a pH value of 8–14, preferably 10–12.

Particularly preferable is that the LD(PLP=LPL) reaction product be subjected to molecular separation to obtain an LD fraction, preferably by means of low-pressure ultrafiltration through alkali-stable ultrafiltration membranes with a nominal cut between 18 and 38 kD. In addition, the LD (PLP=LPL) reaction product is subjected to an exchange of the alkali ions by means of an artificial resin cation exchanger in the hydrogen form until reaching a stable pH value in the area of 4 to 6.8, preferably 5–6. Afterwards the acid LD (PLP=LPL) fraction has the pyrogens removed by filtering and then it is, for example, sterilized by means of autoclaving, for example, at 121° C. for 14 minutes.

The aqueous solution of the reaction product (PLP=LPL) is processed in the usual way, if necessary with inactive ingredients, to a fluid pharmaceutical preparation depending on the form of administration desired. For example, it can be processed with an ointment foundation to produce an ointment for external application or with a basic solution to produce a solution for injection or external application.

The aqueous solution of the reaction product LD(PLP=LPL) can also be processed in the usual way to ampoules for injection purposes. One preferred use of the active substance group is as a virus-inhibiting active substance group for parenteral or local administration to combat viral infections where the viruses can be among others retroviruses, particularly of the HIV type (AIDS viruses).

It can also be advantageous to use the active substance group of the present invention in the form of a chelate of noble metals like Pt, Au, or Pd.

Other advantageous developments of the invention follow from the secondary Claims.

Long-term tests on human subjects have shown that parenteral daily administrations of 2–7 ampoules at 2 mg of active substance/24 hour are able to cure severe influenza infections (also as viral-bacterial mixed infections) within 24 to 48 hours. Even severely asthmatic patients suffering from severe influenzal infections can be so strongly influenced by 10 mg/80 kg body weight/24 hours without the use of corticosteroid doses over 5 mg that the dangerous status asthmaticus can be avoided.

In experimental bronchiospasm in animals, an effect of atoxic doses (parenteral) in the sense of an inhibition of the bradykinin spasm (serotonine inhibition and inhibition of prostaglandin synthesis) has been established.

These effects are extremely unusual for a chemotherapeutic agent and they show that this active substance system comes closer to meeting M. LANGE's demands (see above reference) than the previous HIV inhibitors.

Some special advantages of the invention are as follows:

In the HIV-infected cell culture (human+lymphocytes) (for test, see below), a significant inhibition of syncytia formation ("anti-HIV activity") occurs in the region of non-cytotoxic concentrations.

In cell culture systems from central neurons (from the hippocampus or cortex) under stringently controlled test conditions, a significant increase in survival capability ("survival effect") both of artificially damaged and non-damaged neurons occurs which is biologically comparable with an inhibition of escalatory cellular processes (additional restitutive effect).

Because neurons are obviously a preferred target organ both for HIV and conventional viruses (in situ on patients), this property is of particular curative importance.

Orientational tests derived from the field of basic M. Parkinson research show among other things that it is very likely that the active substance group is capable of passing through the blood-brain barrier.

Even with long-term medication (sc) over a period of years, no undesirable sensitization occurs. There are no general reactions to the medication like, for example, reactive fever, and the blood picture does not deteriorate in any way related to the medication.

With infections caused by conventional viruses (influenza, varicella, etc.), there is rapid and complete restitution with defervescence without undesirable side effects on circulatory efficiency.

Because a non-protein active substance is involved, it functions neither as a co-antigen nor as a pyrogenic substance.

Parenteral medication is simple and problem-free (sc).

The curative doses with ARC patients are 20–40 mg/week.

Even in the case of the most extreme overdosage (e.g. 48 mg/24 hours, repeated), neither acute nor chronic secondary damage of a local or systemic nature occurs.

Primary emphasis/indication areas for the new active substance system—without however being restricted solely to these areas—are as follows:

HIV infections

ARC cases with opportunistic infections

Cell damage through chronic virus infections in general

Curative influence on the occasional multiresistance of cancer cells against conventional antitumour chemotherapeutic agents Diseases of the central nervous system Before the invention is explained in more detail, the abbreviated names and other abbreviations used are first presented to facilitate later understanding.

| | |
|---|---|
| LD = | Low dalton (low-molecular-weight, here max. 3000 D) |
| HD = | High dalton (high-molecular-weight, here: >3000 D) |
| P = | Polysaccharide chains, natively bound on lignin units or with polysaccharides as intermediate links between lignin and cellulose. |
| L = | Lignin units (native) in all natural variants |
| LD-L = | (Low dalton lignin units - max. 3000 D) |
| HD-L = | (High dalton lignin units) |
| (PLP) = | Lignin units high in saccharides as they are extractable as milled-wood lignin from, for example, wood meal with water at an alkaline pH, and also in variations produced through wood biosynthesis. |
| (LPL) = | Lignin units (polysaccharides) low in saccharides as they are extractable from xylem incarbonization products like lignite, coloured coals (up to hard coals) by means of alkaline polar aqueous media but which through the process of incarbonization are strongly depleted of assimilable energy carriers of the polysaccharide type (e.g. because of microbial breakdown before the incarbonization) |
| LD (L-PL) = | Lignin units low in saccharides, like those produced by incarbonization processes, as they are extractable with, for example, alkaline aqueous media but which through the process of incarbonization are strongly depleted of assimilable energy carriers of the polysaccharide type, with low dalton (soluble also at a pH under 7.0). |
| LD (PLP) = | Low dalton fraction of lignin units high in saccharides (see above). |
| HD (LDP ≡ PLP) | Reaction product from LD units derived from L units high in saccharides and LD units derived from L units low in saccharides |
| LD (PLP ≡ LPL) | The low dalton fraction of the above-mentioned reaction product which is suitable for the biological application described in the invention. |

The studies which have been carried out show that the reaction product (LPL=PLP) of the present invention develops a virucidal effect and on the other hand, it is practically free of side effects.

An advantage of the saccharide-chain active substance group of the present invention is that a "non-protein" is involved which doesn't activate the immune defense against exogenous proteins, and it is therefore suitable for long-term medication.

It is presumed that the invented active substance group prevents the docking and attaching of a virus, in particular an HIV virus, to a host cell. It is highly likely that an artificial glycoprotein which isn't a real protein will not elicit a negative immune reaction—it even functions in the most sensitive system, an isolated brain cell, as a "survival factor".

In curative doses (0.1 mg/kg body weight in humans), in the case of long-term administration as well, the active substance group does not have a sensitizing effect, it is non-toxic, and it has no side effects. The active substance group of the present invention possesses hydrophilic domains which causes very good aqueous solubility.

In summary, it can be stated that the substance group is of the present invention substance group is suitable for long-term administration for reasons of its non-protein structure and its non-toxicity.

A particular advantage of the active substance group of the present invention is that it can protect nerve cells in the sense of being a survival factor.

One very special advantage of the active substance group of the present invention is its diversity which means that always the most diverse active substance conformations and charge distributions are offered to the virus.

It is known that many viruses, in particular the HIV viruses, change and adapt exceedingly rapidly so that a single conformation is no longer efficacious against a mutating virus.

The glucolignin units described herein are complicated polysaccharide polyose lignin system "networks" which for reasons of their steric- and charge distribution-related diversity can neutralize a wide variety of glucoreceptors. The active substance group described herein (low-molecular-weight and aqueous soluble) consist essentially of saccharide chain-depleted (i.e. polysaccharide chains) phenylpropane units with quinoid domains (ortho- or paraquinoid).

Lignoid molecular domains which have an affinity for saccharide lateral chains and are partly depleted in a steric-specific way in glucomolecules are found in nature in so-called incarbonization products; therefore in coloured coals, lignites, and also in trace amounts in hard coal. During the course of incarbonization over millions of years, a depletion of the polysaccharide chains (e.g. polyoses) occurred which form the biological linkage between the lignin units and the cellulose. This occurred through microbiological breakdown, oxidative long-term conversions, etc. which lead to a carbohydrate-depleted incarbonization product.

An additional advantage of the invention is that the molecular system is capable of biologically penetrating cell membranes, as could be experimentally proven by means of measurements on nerve and liver cells in situ.

Scientific studies have established that the effect of the active substance group on infected cell cultures is surprisingly significant and no substantial toxic side effects occur.

Consequently, the active substance group is suitable for long-term medication. No loss of efficacy occurs with long-term administration. It can be administered without risk in suspected cases. And it can be combined with appropriate kinds of nonspecific active substances. In general, it shows a restitutive effect and it can be injected without problems.

In the following sections, the invention will be explained in more detail by means of production examples and accompanying figures. The invention should however by no means be restricted to those presented here. The figures are as follows:

BRIEF DESCRIPTION OF THE DRAWINGS

FIG. 2a–2e: Fluorescence spectra for solutions of the active substance group of the present invention or its precursors in accordance with example 1 in water.

FIG. 4 shows the survival of living cells in percent after 24 hours in culture.

DETAILED DESCRIPTION OF THE INVENTION

EXAMPLE 1

Figure 1A:
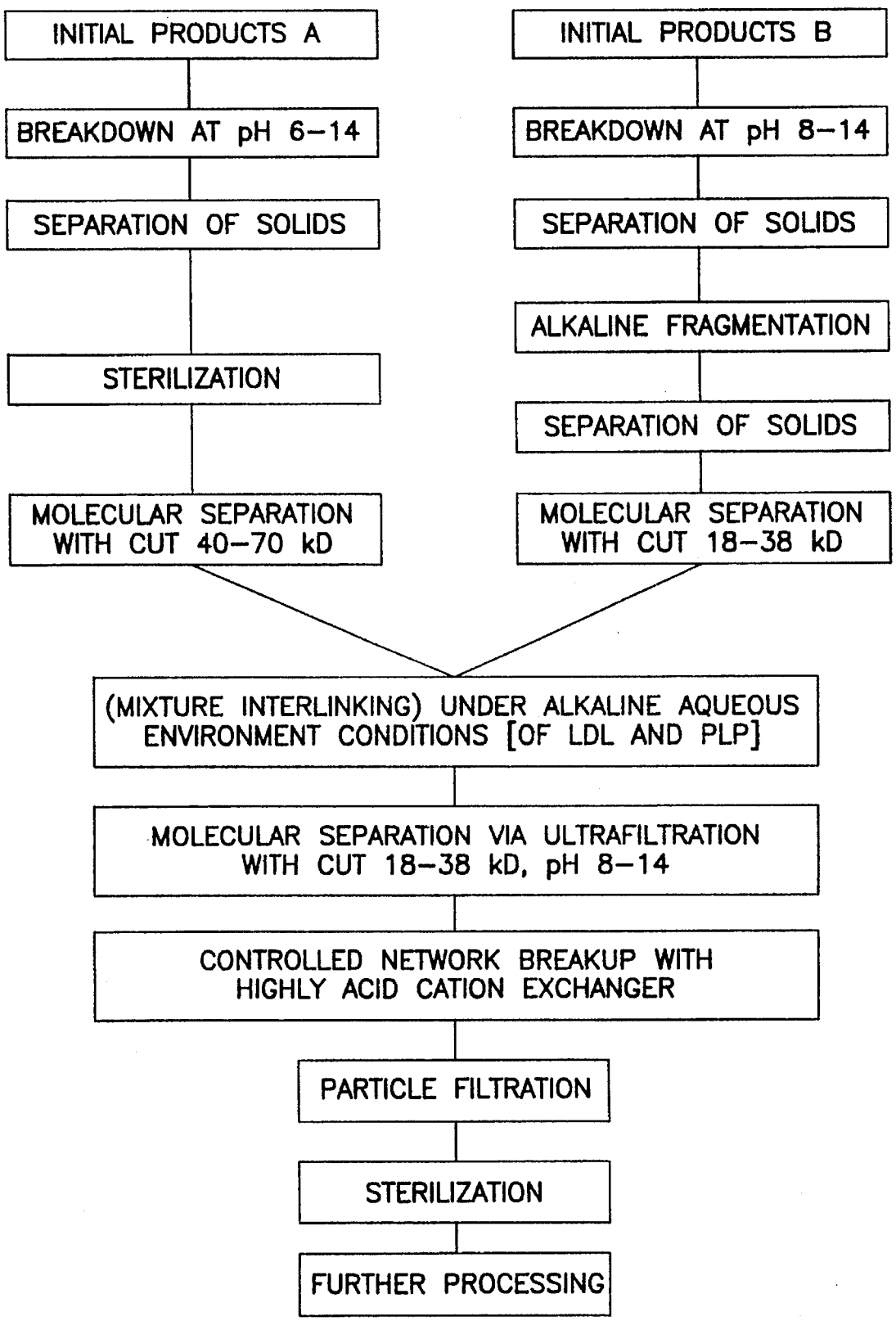
FIG. 1a: A production scheme for an active substance group in accordance with the invention.

Production of an Active Substance Group in Accordance with the Invention

Step 1

Production of the Lignin Fraction High in Saccharides (PLP)

300 g of ground Siberian larch heartwood (*Larix sibirfiaca*) is dispersed as milled wood under agitation in 6000 ml demineralized water, and 150 g KOH is added. This preparation is kept under agitation for 3 days at 46 to 66° C. (dielectric, intermittent heating). Subsequently the solids are separated off with a vacuum filter, the residue discarded, and the filtrate centrifuged until clear and slowly adjusted to pH 11.5 under conditions of constant pH control by means of a calibrated glass electrode by adding portions of a highly acidic artificial resin ion exchanger (Amberlite IR 120) in the hydrogen form, which has been freshly reactivated. The ion exchanger is separated off and discarded. Pyrogen substances and particles are removed from the clear, gold-yellow solution through molecular separation by means of ultrafiltration with alkali-stable ultrafiltration membrane with a nominal cut of 100,000 dalton. From this clear yellow matrix solution, a sample of 20 µl is taken, diluted and mixed with 3 ml of water in a quartz cuvette (1 cm) for spectral purposes, and a series of fluorescence excitation spectra with the following wavelengths are recorded: 450 nm, 490 nm, and 520 nm.

The fluorimeter is adjusted with regard to sensitivity so that the relative fluorescence emission with the 450 nm wavelength is equal to or somewhere in the region of 100. Then the excitation spectrum is recorded at 450 nm (recording instrument 2 cm/minutes, exciting wavelength advance speed 100 nm/min, instrument: KONTRON (SWITZERLAND), Type SFM-23).

For purposes of control, the excitation spectrum is recorded at 490 nm and at 520 nm. A yellow PLP matrix solution was obtained.

Step II

Production of the Lignoid Fraction Low in Saccharides (LPL)

600 g of a "milled" (finely ground) lignite is dispersed under agitation at room temperature (20 ° C. in 10,000 ml of a 1.68 % by weight KOH solution), partly dissolved, separated after 9 hours from solids in a high-speed centrifuge, and the residue discarded. After 24 hours, another solid separation in the high-speed centrifuge is carried out and the solids are discarded. After an alkaline fragmentation over 5 days at 20° C., the centrifugate which has been obtained is once again subjected to solid separation and then a molecular separation through an ultrafiltration unit with alkalistabile ultrafiltration membranes with a nominal cut of 30,000 dalton. The ultrafiltration is stopped as soon as 6.7 liters of flitrate have been obtained. The ultrafiltrate is adjusted to a pH of 5.5 with a freshly activated, highly acid ion exchanger (Amberlite IR 120) using a calibrated glass electrode.

This weakly acid solution is immediately filtered in an ultrafilter to eliminate the pyrogens. Afterwards it is thermally sterilized in an autoclave at 121 ° C. for 15 minutes. Samples are taken to determine the solid concentration and they are compressed at a temperature of 85° C. until weight constancy (infrared radiator). After adjustment to the desired concentration, the ultrafiltrate obtained in this way is used for reaction with the product of step 1 as LPL fraction or conformation modulator (see above).

The C13 spectrum of the LPL fraction (product of step 2) is discussed in the following section:

13C NMR Spectra

The 13C NMR spectrum of the sample is distinguished above all by its high number of carboxyl groups of natural lignin which are indicated by a moderate multiplier at approx. 168–180 ppm. Because of lacking NOE effects and spin-spin interactions with directly bound hydrogen nuclei, the carboxyl C atoms should yield particularly weak signals so that their concentration must have been higher than the relative intensity of their signals. The same is also true for the alpha carbonyl C atoms which absorb in the area of 190.5–198 but show considerably weaker intensities. The sharp singlet at 158.2 ppm can be best attributed to the carbon atom 4 in the p-hydroxyphenyl groups (for labelling of the C atoms see H. D. Lüdemann and H. Nimz, Makromol. Chemie, 175, 2409 (1974)). However because the measurements of the relevant model substances were carried out with hexadeuteroacetone as the solvent and with an internal standard (H. D. Lüdemann and H. Nimz, Makromol. Chemie, 175, 2393 (1974)), perhaps the more probable C atoms 3 and 5 in the syringyl residues should be considered for this signal.

The wide multiplet (7) in the area of 93–145 ppm must be attributed to the carbon atoms 1,2,5, and 6 in the guaiacyl residues and 1,2,4, and 6 in the syringyl residues. The poor resolution of the spectrum indicates strong condensations in the lignin resulting from its preliminary treatment.

In the area of the aliphatic carbon atoms, signals (8), (9), and (15) can be classified as typical lignin signals of arylglycerin-p-arylether compounds, which is the most important type of compound in all lignins. However there is some uncertainty in the classification here because of the solvent and external standard. The relatively weak methoxyl signal at 58.6 ppm indicates a partial demethoxylization during the preliminary processing of the sample. The well-structured signals (10), (11), and (12) which also appeared in this area are not found in typical lignin spectra (H. D. Lüdemann and H. Nimz, Makromol. Chemie, 175, 2409 (1974)). They indicate condensed carbohydrate components.

It is also difficult to explain the wide multiplet (17) in the area of about 0–55 ppm. Here primarily aliphatic carbon atoms should absorb which are not directly bound to oxygen. In lignin, however, there are very few atoms of this kind like, for example, the 13 carbon atoms in pinoresinol units and alpha carbon atoms in dibenzyl tetrahydrofurane units (references: H. D. Lüdemann and H. Nimz, Makrotool. Chemie, 175, 2393, 1974; H. D. Lüdemann and H. Nimz, Makromol. Chemie, 175, 2409, 1974). These kinds of carbon atoms (e.g. in $CO-CH_3$, $-CHOH-CH_3$, or $-CH_2-C$) must have either originated during the oxidative or other phases of the preliminary processing of the lignin or were already present during the lignin preparation from the wood material.

In summary, it can be stated that the present sample consists of a structurally greatly changed lignin whose lignin character can no longer be clearly identified. The classification of the signals is made more difficult by the use of $D_2O$ as a solvent because it is not soluble in the hexadeuteroacetone in which the comparison lignins were measured (H. D. Lademann and H. Nimz, Makromol. Chemie, 175, 2409 (1974)). In addition, the use of an external instead of the internal standard can slightly influence the chemical shifts so that differences in the chemical shifts of approx. 2 ppm can occur.

13C chemical shifts in ppm from TMS as an external standard, recorded in $D_2O$ with a Varian XL-100-15 spectrometer.

| No. | Delta (ppm) | Intensity | Classification*) |
|---|---|---|---|
| (1) | 190.5–198 | weak multiplet | alpha carbonyl and cinnamic aldehyde groups |
| (2) | 168–180 | moderate multiplet | carboxyl groups |
| (3) | 164.0 | weak | |
| (4) | 158.2 | strong singlet | C-4 in p-hydroxyphenyl (C-3/5 in syringyl?) |
| (5) | 150.5 | weak | C-4 in guaiacyl |
| (6) | 148.5 | weak | C-3 in guaiacyl |
| (7) | 93–145 | wide multiplet | C-1/2/5/6 in guaiacyl and C-1/2/4/6 in syringyl |
| (8) | 88.4 | weak | C-β in arylglycerin-β-arylethers |
| (9) | 70.0 | moderate | C-alpha in arylglycerin-β-arylethers (?) |
| (10) | 67.9 | moderate | |
| (11) | 67.4 | moderate | |
| (12) | 66.2 | weak | |

-continued

| No. | Delta (ppm) | Intensity | Classification* |
|---|---|---|---|
| (13) | 64.8 | strong | C-gamma in phenylcoumarins and C-gamma and C-β in β-1-dilignol units |
| (14) | 63.8 | moderate | C-gamma in cinnamic alcohols and arylglycerin-β-arylethers with alpha carbonyl |
| (15) | 60.7 | moderate | C-gamma in arylglycerin-β-arylethers |
| (16) | 58.6 | moderate | $OCH_3$ |
| (17) | 0–55 | wide multiplet | aliphatic C atoms, preferably not bound to oxygen |

*)see here: H. D. Ludemann and H. Nimz, Makromol. Chemie, 175, 2409 (1974)

Further Processing in Step III

By the stepwise addition of the conformation modulator (see below) in a specified concentration of 2 mg/ml, the 520 nm excitation spectrum is recorded in steps of 5 μl additions in the 3 ml quarz cuvette ("fluorescence titration") until the addition increase is such that a significant peak at 465 nm appears and the emission over the whole emission wavelength area strongly increases and the 394–396 nm emission increases around the order of magnitude of an 80% relative emission. The quantity of conformation modulator which is necessary for this fluorescence increase via the conformation modulator admixture is determined (e.g. here it was 10 μl of the 0.2% solution) and multiplied by the factor 2.5.

The admixture quantity of conformation modulator solution which is determined in this way is then added to the available quantity of matrix solution: For example, in accordance with the instructions, 5000 ml of the 0.2% conformation modulator solution is added to 4000 ml of the matrix solution of this preparation (120 μl matrix requires 10 μl of 0.2% conformation modulator solution, therefore after multiplication by the factor 2.5, a 4000 ml matrix yields 2000 times 2.5). At 45° to 65° C., the solution is intensely mixed and after 4 hours reaction at 45° to 65° C., it is subjected to a molecular separation in an ultrafiltration unit with an alkali-stable ultrafiltration membrane with a nominal cut of 30 kD. Then the residue is discarded and the flitrate is processed further. By means of a highly acid cation exchanger in $H^+$ form, the flitrate is adjusted to a pH of 5.5 and immediately thermally sterilized after filtering to remove the pyrogens.

From the batch, samples for biological and analytical purposes are taken and after identity testing using fluorescence spectroscopy and testing for absence of pyrogens, it is released for the production of ampoules. A 0.9% NaCl solution sterilized for injection purposes serves as the solvent for ampoules used for parenteral administration.

Figure 2D:
Figure 2E:
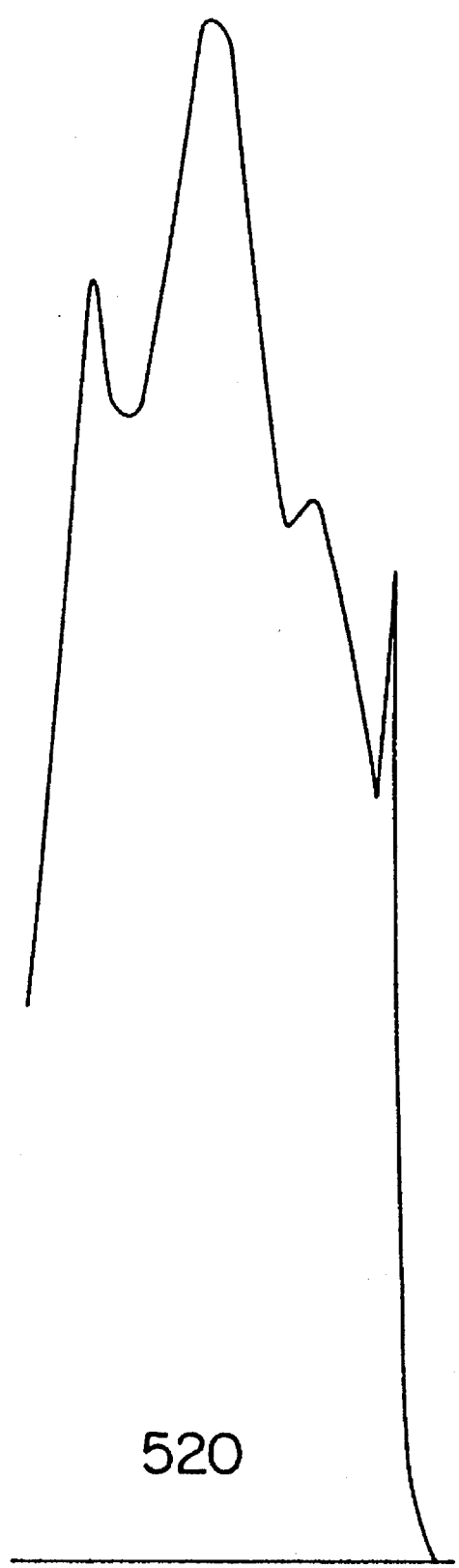
Figure 3:
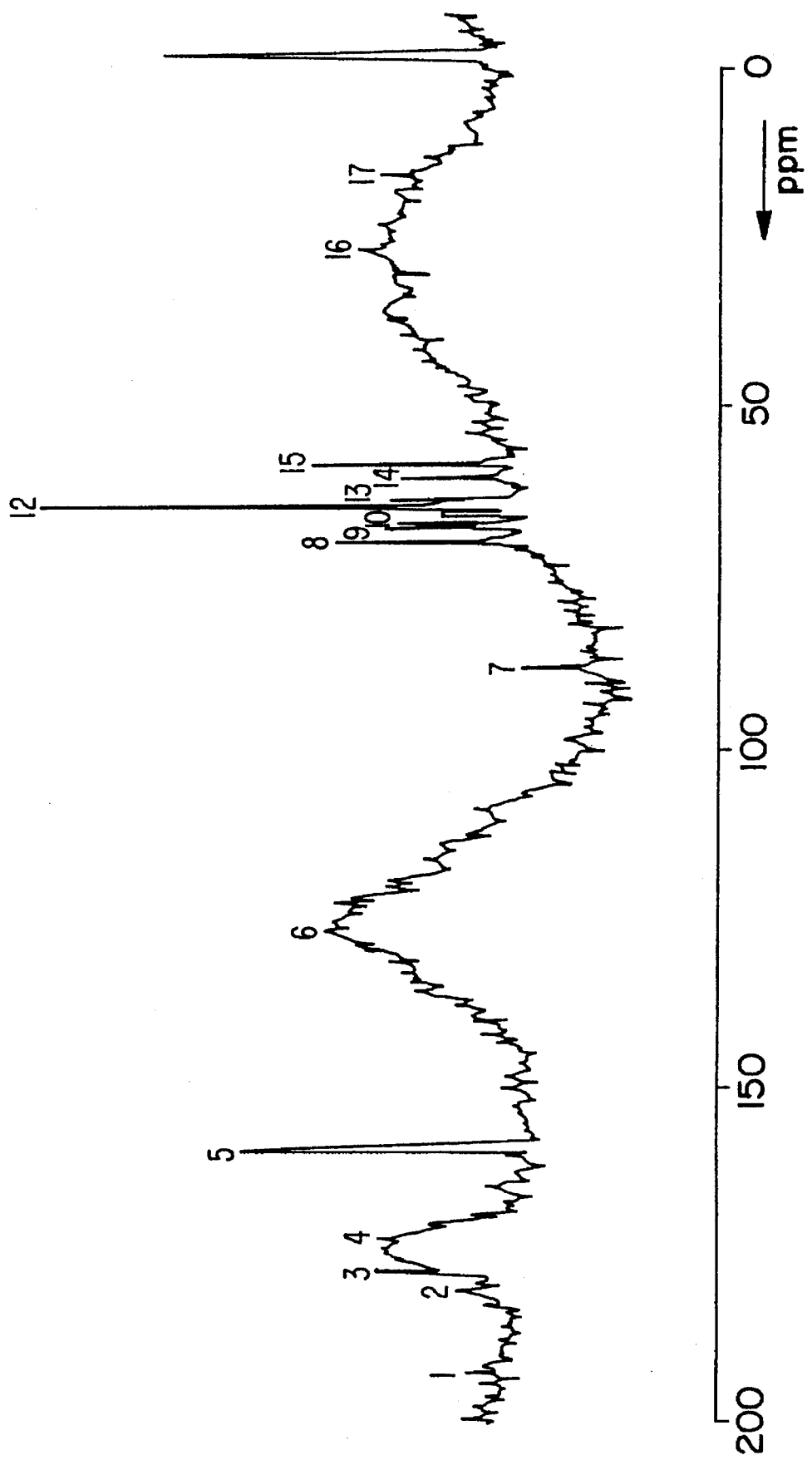
FIG. 3: A C13 spectrum of a variant of the active substance group of the invention.

In FIG. 2a to 2c, the fluorescence excitation spectra of the PLP solution at exciting wavelengths of 450 nm, 490 nm, and 520 nm (substance group A) are shown. In accordance with the principle of fluorescence titration, FIGS. 2d and 2e show at an exciting wavelength of 520 nm the measurable influence of the addition (here two-step) of PLP in 5 μl steps: Crucial here is the occurrence and height of the emission peak at an exciting wavelength of 466 nm.

For purposes of clarification, the reaction scheme is presented FIG. 1a.

Figure 1B:
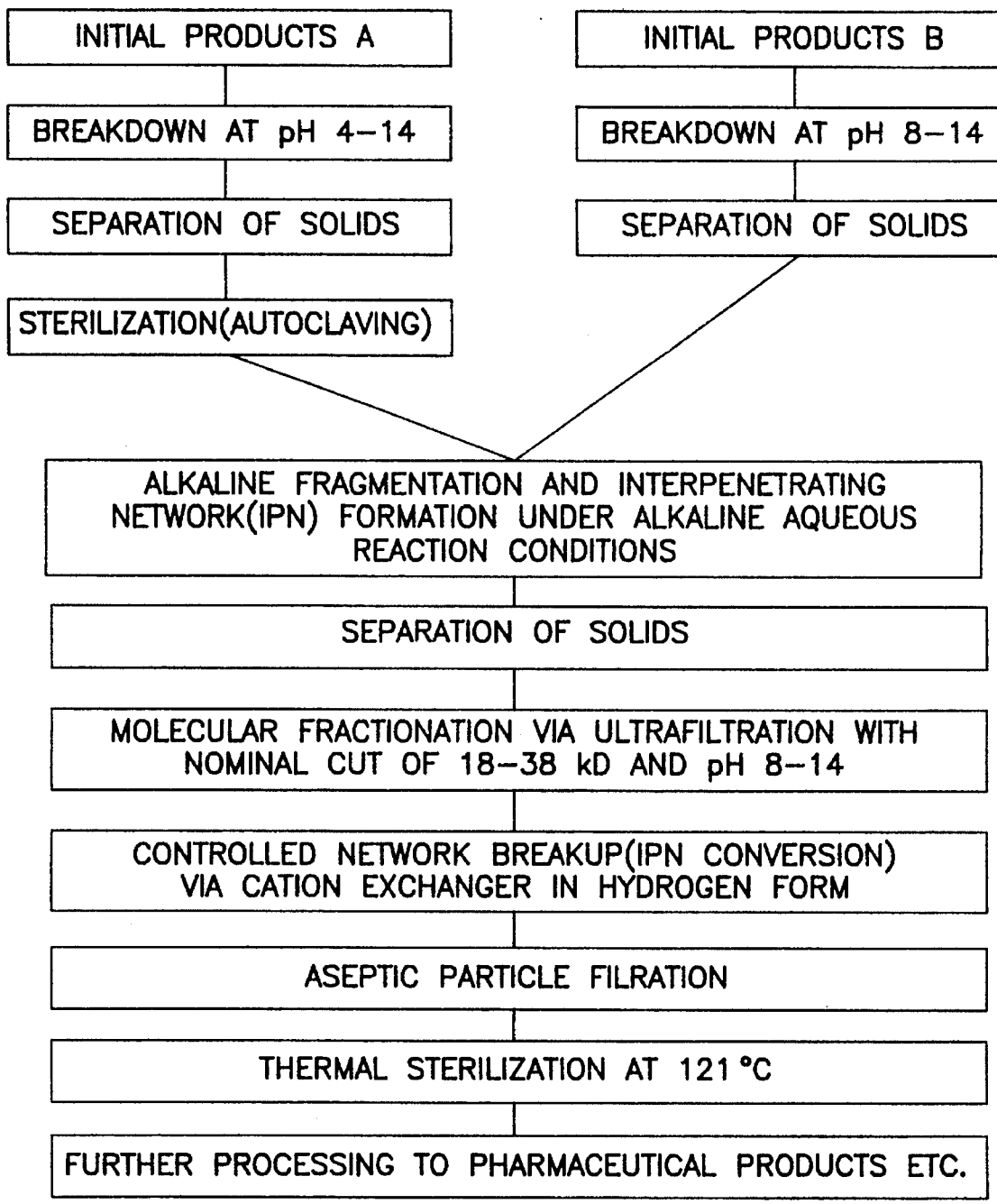
FIG. 1b: An additional scheme for the production of an active substance group in accordance with the invention.
Figure 1C:
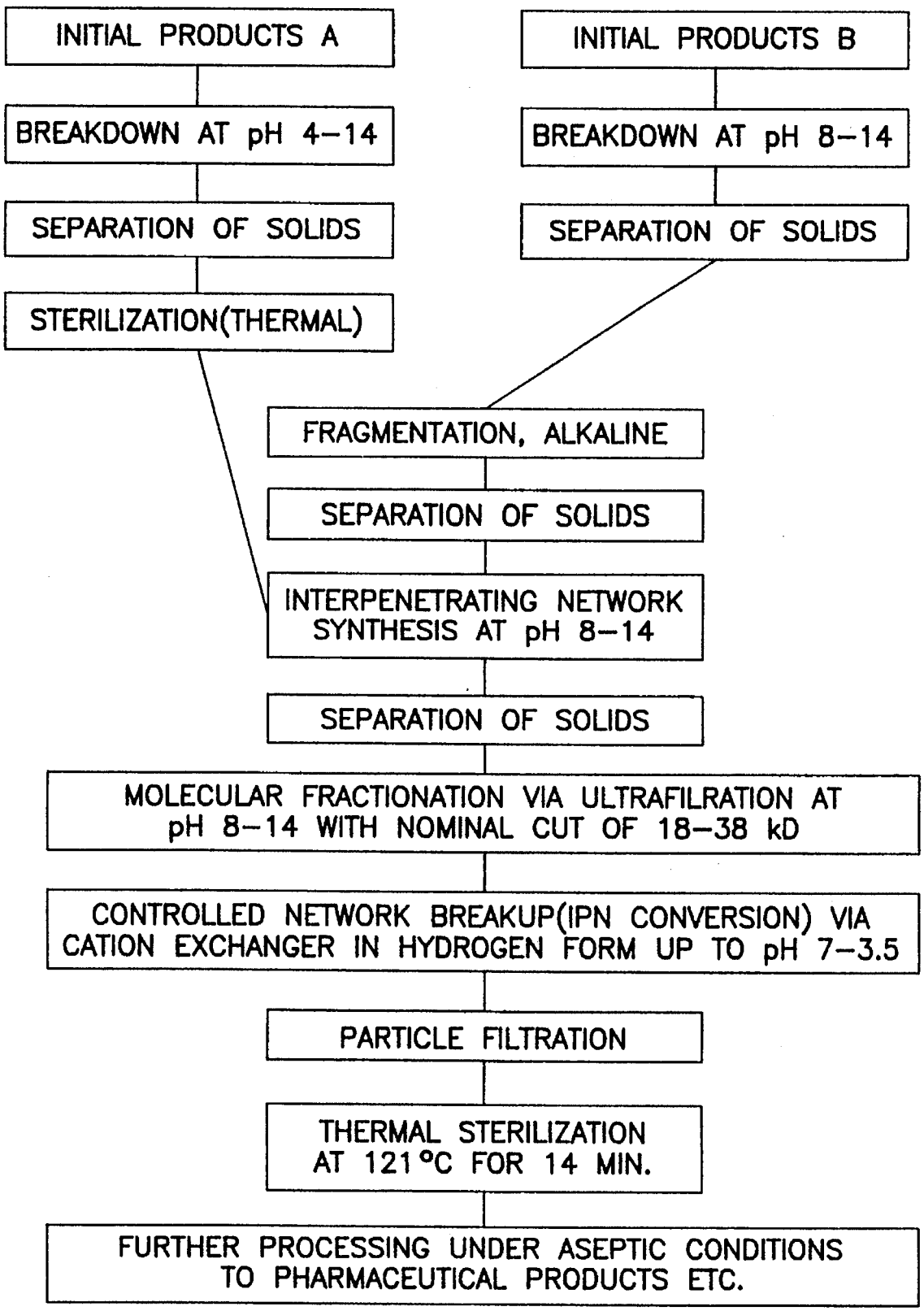
FIG. 1c: A schematic diagram showing a further variant of the production of an active substance group in accordance with the invention.

Possible modifications of this procedure are shown in FIGS. 1b and 1c.

EXAMPLE 2

Production of an Active Substance Group in Accordance with the Invention

Production of the Lignin Fraction High in Saccharides (PLP)

180 g of ground Siberian larch (*Larix sibirfiaca*) heartwood triturated to a particle size of 0.05 to 0.315 mm in a beater mill which has extract substances removed by extraction with ethanol/benzene and ethanol before extraction in aqueous medium (TAPP-Standard T-12m, 1959), and 120 g European beechwood (*Fagus sylvatica* L), prepared in above manner, were mixed and processed in an analogs way to example 1. Whereas *Larix sibirfiaca* heartwood contains arabogalactan (4 parts galactose: 1 part arabinose), beech xylan chains containing oxymethyl glucuronic acid and L-arabinose are present. As a result, the properties of the end-product are modified accordingly.

The milled-wood modification is processed as described in example 1 with the extraction being carried out in accordance with BECKMANN and LISCHE; Angewandte Chemie 34, 285 (1921): Here the extraction is carried out with 1M KOH in an autoclave at 121° C. for 3.5 h.

EXAMPLE 3

Production of an Active Substance Group in Accordance with the Invention

I) Production of the Lignin Fraction High in Saccharides (PLP).

The PLP production is carried out as in example 2.

II) Production of the Lignin Fraction Low in Saccharides (LPL).

LPL is produced from pulverized Eocene brown coal instead of the lignite used in example 1. Otherwise the production is carried out as described in example 1.

EXAMPLE 4

Production of an Active Substance Group in Accordance with the Invention

I) Production of the Lignin Fraction High in Saccharides (PLP)

210 g of larch heartwood, 60 g of beech heartwood, and 30 g fruit skin from *Prunis avium* were processed as described in example 2.

II) Production of the Lignin Fraction Low in Saccharides (LPL)

Miocene brown coal which was purified in the usual way by Soxhlet extraction with benzene from resins, fats, and waxes was processed as in example 1.

EXAMPLE 5

Production of an Active Substance Group in Accordance with the Invention

I) Production of the Lignin Fraction High in Saccharides (PLP)

210 g larch heartwood and 90 g synthesized wood in accordance with Freudenberg (Freudenberg K., Harkin J. M., 1960, Models for the Binding of Lignin on Carbohydrates, Chem. Ber. 93, 2814–2819) were processed to PLP using the procedure described in example 2. The rest of the processing is carried out as in example 1.

EXAMPLE 6

Production of an Active Substance Group in Accordance with the Invention

An alkali-obtained extract (A5) from chlorite holocellulose, derived from beechwood powder (*Fagus sylvatica L.*), delignified with $NaClO_2$ (in accordance with Feckl, 1981, dissertation from the University of Munich) and alkaline extracted with a 4% KOH solution in accordance with FENGEL (1976, Holzforschung 30, pp. 73–78), was subjected to a separation of solids, sterilized, and fed into the LPL solution derived from lignite (produced as in example 1) in a quantity of 900 ml (concentration: 0.12% solid content, lignin residue content: 2.3%) at the beginning of the third day. The volume of the 2.1% solution (pH 11.4) was 9100 mi. The fragmentation time was 9 days. The solution was then processed as described in FIG. 1*b* during which a separating off of the solids was subsequently carried out and the remaining solution was subjected to a molecular filtration via ultrafiltration with alkali-stable membranes with nominal cut value limits of 18–38 kD and a pH value of 8–14. Afterwards the solution was acidified by means of $H^+$ ion exchanger and subjected to an aseptic particle filtration. The flitrate obtained was thermally sterilized in an autoclave at 121° C., and it could then be processed further as described in example 1.

EXAMPLE 7

Production of an Active Substance Group in Accordance with the Invention

Step 1:

100 g ground (like "milled wood") cinnamon bark is extracted for 6 days at 60° C. with 1000 g of a solution of KOH in demineralized water (pH adjustment to 8–9 with KOH). During this process, a circulation of the material was maintained by means of oxygen introduction. Afterwards the solids were separated off by centrifuging and discarded. The PLP solution obtained in this way was thermally sterilized in an autoclave and simultaneously transferred together with the LPL product of step 2 of example 1 into an alkaline medium under heated conditions. The further processing was carried out as described in example 1.

This preparation method is summarized again in FIG. 1*c*.

EXAMPLE 8

600 g of milled colored coal (Eocene) identical with the product from example 3 is broken down under alkaline conditions at room temperature in 10 l of solution of 110 g KOH and 60 g NaOH in demineralized water over 2 to 5 hours under agitation. Before the dissolution of the hydroxides, 20 g of highly mechanically-dispersed activated charcoal is added to the water. This activated charcoal portion is separated off along with the sediments by the following preliminary centrifugation and, therefore, it represents a preparatory step in purifying the product which will be used later for fragmentation, etc.

The preliminary centrifugation in high-capacity centrifuges, of if need be in beaker centrifuges, for example at 4000 to 5000 r.p.m., is required because the separation of solids (next step in procedure) with a maximal gravity effect by means ultracentrifugation (also high-speed centrifuges with vertical separation cylinders and approx. 40,000 r.p.m.) comes immediately to a standstill if the quantity of the sediment lowers the efficiency in the purification cylinder. This would make industrial production impossible. The preliminary centrifugate is collected, mixed with 8 g activated charcoal per 10 l, and immediately subjected to ultracentrifugation, circulatory if necessary, until the purification cylinder of the centrifuge remains practically clear and only the most minimal traces of a laky sediment can be seen.

This now intensively prepurified product (crude alkaline solution of the active substance) is kept at room temperature and "alkaline autofragmentation" is allowed to take place. On-going pH measurements are made during these fragmentation processes. In addition, further ultracentrifugations like that described above should be carried out on a trial basis at least twice in order to continuously remove the constantly forming sediments of pharmacologically undesirable fragment condensates which are without genuine solubility and molecular reactivity.

After the alkaline autofragmentation (i.e. after about 9 days), superfine purification is again carried out by means of ultracentrifugation and the solution (still highly alkaline) is subjected to a gentle fractionation via ultrafiltration with a nominal molecular cut of 30,000 dalton in such a way that in a production preparation (like the present example) of 10 liters, the ultrafiltration is stopped when approx. 74,000 ml of ultrafiltrate has been obtained and the residue volume is therefore approx. 2000 ml.

The residue is discarded, the ultrafiltration unit is thoroughly alkaline washed, and the flitrate is subjected to the next preparation step. Although this specified step of the invention seems to be of little importance for the conformation status of the end-product, in reality the contact which now takes place between the alkaline salts of the ultrafiltrate and the highly acid artificial resin ion exchanger (in the extreme hydrogen form) is also a process which is of importance for the end-product.

The "acidification" of the alkaline ultrafiltrate through, for example, the addition of acid, and indeed even the use of ion-exchanger columns are completely inappropriate, because in the latter case, for example, the column is easily blocked and a completely unusable flitrate is obtained.

In accordance with the invention, the cation exchange (exchange of the $Na^+$ and $K^+$ ions for $H^+$) is carried out in a batch procedure in a reaction vessel, and the ion removal process is continually electronically monitored by means of a calibrated glass electrode.

The target point is a pH value of 5.1 and after this value has been reached, the addition of the ion exchanger must be immediately stopped. The invention specifies that the deionization be carried out under conditions of continuous circulation of the still partly alkaline product and care must be taken by means of turbulence formation produced, for example, by an adjustable circulation pump that areas with higher ion exchanger concentration are not formed.

Because the conformation profile of the active substance group cannot currently be satisfactorily measured, compliance with even the smallest, experimentally-derived reaction steps specified in the invention remains the most secure method to produce active substance groups which are pharmaceutically identical to that described in the invention.

A sterile filter is used to rid the now cation-exchanged active substance group of particles which could have entered the solution during contact with the ion exchanger, and immediately afterwards it is sterilized in an autoclave (e.g. 121° C. for 20 minutes). This active substance solution can be completely safely stored at plus 4° to 20° C. for 18 months and, for example, it can be used for the production of ampoule solutions (e.g. solvent: 0.9% saline).

The use of activated charcoal at this point is not a nonspecific purification operation. Instead it is a matter of influencing the reaction situation during the course of the specific fragmentation process: In principle, activated charcoal of the "activated charcoal powder p.a." type should be used (example of the detailed characteristics of this kind of activated charcoal: pH value of a 5% solution in water, 20° flitrate, 4.0–7.0; methylene blue absorption capability: 0.15% solution: greater as 12 ml/0.1 g).

Many different functional aspects of the activated charcoal are essential like that, for example, related to its surface oxides content which can confer acidic or basic properties to the activated charcoal. Although they are pure carbon surfaces like with graphite hydrophobics, they form surface oxides in situ in the hydrophilic regions so that the activated charcoal can be moistened by water and therefore exerts an influence on the reaction situation during the course of fragmentation. In addition, the particle size distribution of the activated charcoal is also important: About 50% should be particles which are smaller than 40 micrometers. With this particle size distribution, the activated charcoal additives can be easily separated via technological methods without the use of filtering systems.

EXAMPLE 9

The product described in example 8 which in accordance with the "one-or-more-ions principle" has already had the sediment particles removed several times by ultrafiltration is briefly brought to 46° C. with microwave heating and then left to cool again to room temperature. After a last superfine purification by means of ultracentrifugation (for more details, see example 8), the alkaline product mixture is processed further in the same way as the product was obtained, in accordance with example 8.

Through this repeated, physically-induced change in the processes of fragmentation, the active substance group is modified.

EXAMPLE 10

Reaction photometric studies have shown that therapeutic agents as referred to herein which are produced in accordance with example 8, for example, can be greatly modified by means of photon activation at 388–378 nm. With this substance conversion in the area of the photon receiver units of the active substance group, photochromatic processes occur. These are reversible photochemical reactions by which substance A is transformed into either another form (conformation) or to compound B and these reversible reactions which can proceed either direction are elicited by the absorption of UV or visible light. The therapeutic agents are influenced by the 388 nm wavelength until monitoring of extinction indicates, for example, after 90 minutes, that an extinction maximum has occurred. One can simultaneously use and record the monochromatic 388 nm radiation as measuring radiation in a double-beam photometer (FIG. 6) (e.g. band width of 5 nm).

Figure 6:
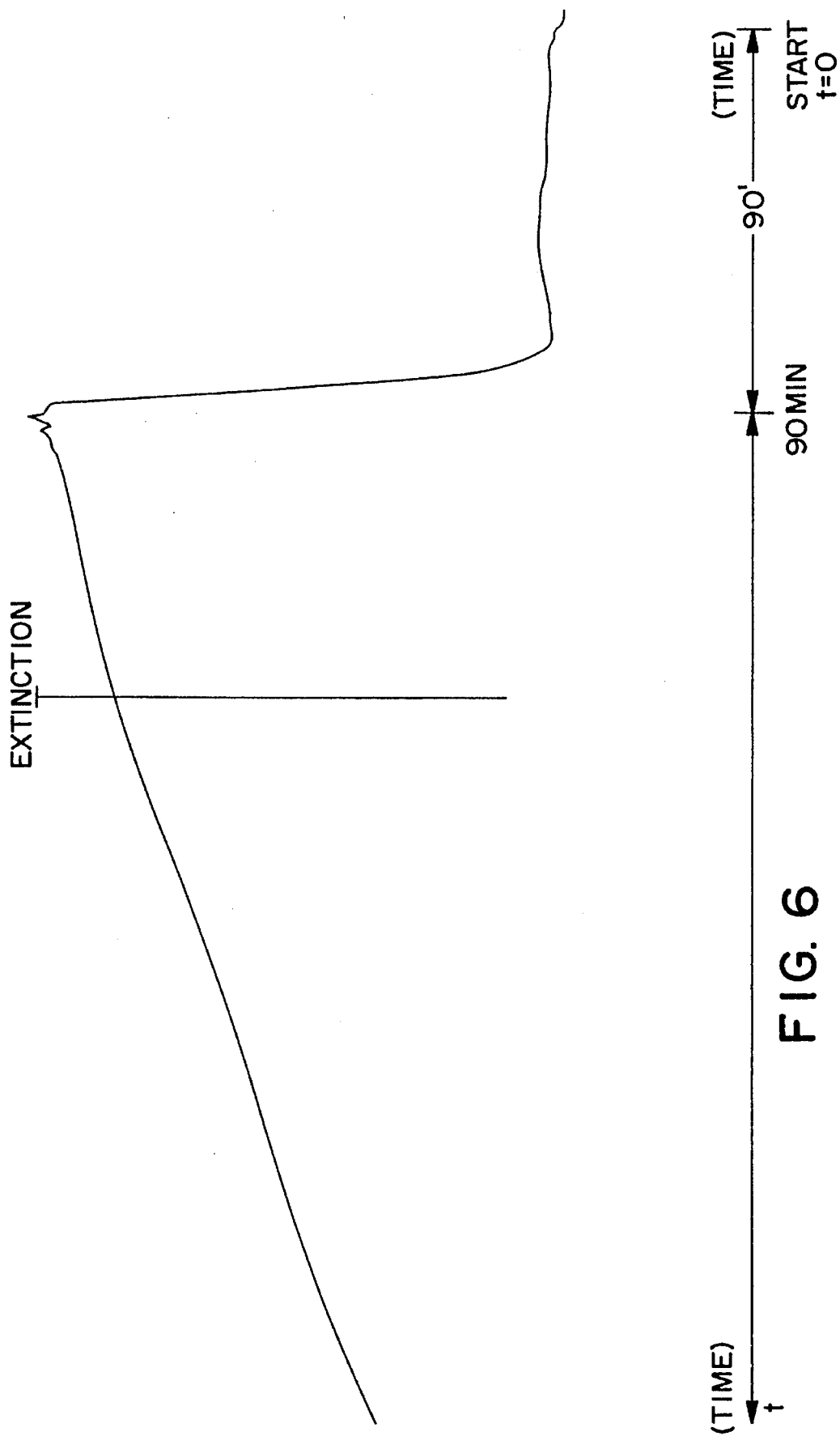
FIG. 6: A graph showing extinction measurements as a function of radiation duration of the active substance solution.

The conditions for generating the data set forth in FIG. 6 are as follows:

Measurement methodology: Double-beam spectral photometer SHIMADSCHU 210 A

DIGITAL INDICATORS+RECORDING INSTRUMENT;

1 cm quartz cuvette, measuring radiation 388 nm, speed: 2 cm/h. Setting ABS 0–0.2, starting absolute value 0.505, slit 8 nm, total measurement time: 24 hours.

Long-term constancy better than 2.0%/24 hours (Grid: 1200 lines/mm, modified Czerny-Turner arrangement)

Measurement temperature: 21° C.

In addition to extinction maximum measurement (see FIG. 6), conformation modulation can also be detected through florescence measurement (recording of the excitation spectrum). Via photochromatic influences on the photon receiver units in the active substance group, a curve is obtained in all excitation spectrofluorimetric areas which is to a great extent different from that of the initial sample. These UV-induced systems increase in a specific way the chemotherapeutic effect in situ or in vivo. Clinical experiments indicate that this UV-activated active substance solution is among other things suitable not only for exerting an affect with AIDS but also to influence the T lymphocytes with T-cell lymphoma. It is known to exert an influence on CTCL through the UV activation of 8-MOP, which is composed of a furane ring and coumarin. The procedure is however very elaborate (leucopheresis), whereas with the UV-activated compound produced in accordance with the present invention, it is only necessary to carry out normal parenteral drug therapy.

In general, it can be stated that the wood extraction conditions have a great effect on the molecular structure of the soluble polysaccharide lignin units. Here the molecular structure of the matrix is dependent in many ways on the initial material and therefore on which tree heartwood or straw or grass is used. To avoid traces of herbicides, old trees must be used.

The type of wood (conifer, broad-leaved tree) and also the part of the plant used as the initial material (nutshells, peach stones, softwood parts) are also decisive. For example, the bond between P and L in nutshells is considerably stronger than in a softwood.

In addition, the method of LD-PLP network extraction is essential for the product. Especially suitable here: alkaline extraction; treatment with hot water or steam under pressure (autoclave), or electrolysis with NaCl as an electrolyte.

The active substance group of the present invention contains therefore many structural units from the natural substance arena and from carbohydrates.

In the following sections, studies which have been carried out on the effects of the material from example 1 on different cell systems will be described.

Test of the Active Substance Group from Example 1 on HIV-infected Human Lymphocytes As a test system, lymphocytes from the umbilical cord blood of neonares were used which had been preactivated for 2 days with 10 µg/ml phytohaemagglutinin (PHA). This cell culture system is a very sensitive lymphocytic system for the study of HIV. Approximately 200,000 PHA-activated cord blood lymphocytes in 1 ml cultures were infected with the HIV-2 isolate, HIV-2ROD (end concentration approx. 200 syncytia-forming units/ml) in the presence of the test substance. An optical microscopic assessment of the infected cultures took place on the third day after infection (examination for the development of virus-induced cell fusions, so-called syncytia).

The active substance group was dissolved in culture medium without subsequent sterile filtration. Concentrations of 200 µg/ml, 100 µg/ml, 50µ g/ml, 20 µg/ml, 2 µg/ml, and 0.2 µg/ml were tested. Two batches (A88-1 and A88-4) were investigated.

| Concentration | Optical microscopic assessment an days 3–4 after infection | |
|---|---|---|
| µg/ml | Syncytia formation | Tolerance |
| Test of batch A88-1 of example 1 in 24-hole plates for inhibition of syncytia formation | | |
| 200 | – | good colonies |
| 100 | – | good colonies |
| 50 | – | good colonies |
| 20 | + | good colonies |
| 2 | ++ | good colonies |
| 0.2 | ++ | good colonies |
| Pos. control | +++ | |
| Test of batch A88-4 of example 1 in 24-hole plates for inhibition of syncytia formation | | |
| 200 | – | good colonies |
| 100 | – | good colonies |
| 50 | – | good colonies |
| 20 | + | good colonies |
| Pos. control | +++ | |

– no syncytia formation
+ isolated syncytia formation (1–10)
++ clear syncytia formation (10–50)
+++ strong syncytia formation (>50)

Assessment of the inhibition of syncytia formation with batch II
Target cells: peripheral lymphocytes (PBL)
Virus: HIV-2ROD, $10^5$ SFU/ml, approx.
1,500,000 cpm/ml/90 min
final dilution used: 1:500

| | Syncytia formation on day | | |
|---|---|---|---|
| Concentration (µg/ml) | 2 | 3 | 4 |
| 1 | + | + | + |
| 5 | + | + | + |
| 10 | +/– | +/– | +/– |
| 25 | – | – | – |
| 35 | – | – | – |
| 50 | – | – | – |
| 75 | – | – | –* |
| 100 | – | – | –* |
| 150 | | cytotoxic | |

*mild cytotoxicity

As can be seen from the table, this batch was effective above 10 µg/ml.

Anti-HIV Activity of the Molecular System
(LABORATORY II)

An active substance group in accordance with the invention was studied in vitro in two concentrations of 2 mg/ml and 16 mg/ml. In this connection, the HIV core protein from laboratory 1, p24, was tested with the antigen capture technique after a primary infection with H9 cells.

Phosphonoformic acid was used as the positive control substance and different concentrations of AZT and ddC were also tested. In this experiment, both samples showed evidence of antiviral activity.

Laboratory 2 uses syncytia formation after a primary infection of MT-2 cells as the end-point.

Test results:

LABORATORY 1

| | % Inhibition of p24 | | |
|---|---|---|---|
| Active substance conc. µg/ml | Adaptogen* 2 mg/ml | Adaptogen* 16 mg/ml | Foscarnet (phosphonoformic acid) |
| 1 | <30 | 30–50 | |
| 4 | <30 | 50–75 | |
| 10 | | | 50–75 |
| 20 | 50–75 | <75 | |
| 50 | | | <75 |
| 100 | <75 | <75 | toxic |
| 500 | toxic | <75 | toxic |
| estimated EC 50 | 15–20 µg/ml | 1–2 µg/ml | <10 µg/ml |

Positive control: AZT and dideoxycytidin (ddC) were each tested with 1–10 µg/ml and showed a >75% inhibition of p24 expression without cytotoxicity.
*Adaption refers to an active substance group according to the present invention

LABORATORY 2

| | % Inhibition of syncytia formation | |
|---|---|---|
| Active substance conc. µg/ml | Adaptogen* 2 mg/ml | Adaptogen* 16 mg/ml |
| 0.1 | 33 | |
| 0.16 | | 14.5 |
| 1 | 50 | |
| 1.6 | | |
| 10 | 82 | |
| 16 | | 88 |
| 48 | | 100 |
| 100 | 100 | |
| 160 | | 100 |
| 500 | somewhat toxic | |
| EC 50 | 1 µg/ml | 1 µg/ml |

Positive control: ddA with 0.25 (90% inhibition) and 2.5 µg/ml (100% inhibition).

It can be seen from the above that the active substance group of the present invention obviously prevents the attack of HIV viruses on cells.

In curative doses (approx. 0.1 mg/kg body weight in humans), the active substance group also does not produce sensitization with long-term administration, it is non-toxic, and it has no side effects. The active substance group of the present invention possesses hydrophilic domains, which leads to good water solubility.

Of course other variations and measures related to the invented principle which are known to the expert are possible in this context like, for example, using other monomers on the surface of the matrix.

Consequently, the active substance group of the present invention is suitable for long-term medication; there is no loss of efficacy with long-term administration; it can be used without risk in suspected cases. In general, it shows a restitutive effect and it can be injected without problems. The above experiment shows that the active substance group of the present invention invention therefore possesses significant antiviral properties.

Test series I (Survival-effect Evidence Without Adjuvant Cellular Stress)

The invented active substance group also possesses however contraescalatory (restitutive) properties as is seen below. Acute disturbances in the central nervous system as they occur, for example, with trauma, brain injuries, ischaemia, etc. are mostly accompanied by degeneration or death of central neurons. Similarly, numerous neurological and neurodegenerative CNS diseases (e.g. Parkinson's, Alzheimer's, and Korsakoffs syndrome) are characterized by the death of selective neuron populations.

For this reason, the study of cell death or survival of central neurons is of great importance. In recent years, research concerning neurotropic factors and neuron-gila interactions has yielded new knowledge related to the survival of neurons in vivo and in vitro. Also included here is new knowledge concerning the importance of membrane lipids—including gangliosides and phospholipids—for the viability of nerve cells. Experiments on nerve cell cultures show that by acting on the membrane lipids, peroxide or oxygen radicals may play a role in survival or cell death.

Materials and Methods

I. Preparation of the Hippocampus Neuron Culture

The hippocampi of 17-day-old rat embryos were dissociated by means of a trypsin/EDTA treatment and mechanical scissors and then plated-out on polylysine-coated coverslips. After an attachment phase in 10% serum, the cells grow in a specified, serum-free medium.

II. Fluorescence Test

Two fluorescent stains are employed in combination so as to colour the living and dead cells differently. Fluorescein diaetate (FDA) is initially taken in a non-fluorescent form into living cells, hydrolyrically split, and converted in this way to a fluorescent compound (fluorescein). Ethidium bromide (EtBr=international generic name for 3,8-diamino-5-ethyl-6-phenylphenathridinium bromide) remains excluded from living cells and only penetrates into dead cells where it fluoresces red in the nucleus.

| Media |
| --- |
| DMEM (Dulbeccos Modified Eagles Medium), Seromed, Munich |
| FKS (fetal calf serum), Seromed, Munich |
| 10% in DMEM (½ hour at 56° C. inactivated) |

| HM (hormone mixture) | |
| --- | --- |
| Insulin | $8.8 \times 10^{-7}$M |
| Transferrine | $1.1 \times 10^{-8}$M |
| Triiodothyronine | $3 \times 10^{-10}$M |
| Hydrocortisone in DMEM | $2 \times 10^{-8}$M |

| Active substance concentrations | | |
| --- | --- | --- |
| The ampoule contains a 2 mg/ml solution. | | |
| Dilution with DMEM | | End concentration in medium (100 µl/2 ml) |
| 1:10 | 200 µg/ml | 10 µg/ml (1) |
| 1:100 | 20 µg/ml | 1 µg/ml (2) |
| 1:1000 | 2 µg/ml | 100 ng/ml (3) |
| 1:10,000 | 200 ng/ml | 10 ng/ml (4) |
| 1:100,000 | 20 ng/ml | 1 ng/ml (5) |

After the attachment phase, the solution was added to the medium surrounding the attached cells in concentrations (1)–(5). Vitality test after 48 hours. From each of 3 cultures per condition, 15 fields with approx. 50 neurons/field were counted.

Result

The vitality test shows a positive influence in a concentration area around 100 ng/ml on the survival of the neurons in the culture in comparison to the control. At 10 µg/ml, a mild toxic effect occurred.

It must be considered when assessing the survival effect that the cells are growing under optimal conditions, which means that no substantial improvement in survival can be expected. Therefore it seems reasonable to carry out experiments under suboptimal conditions (test series II).

Vitality Test with Hippocampal Neurons After 48 Hours in Vitro

Proportion Living/dead Cells

Test Series II

Influence on the Survival of Neurons After Damage

Using microcinematographic methods, it was observed that cells in the microscopic field which were long exposed to the light of a halogen lamp die sooner than those outside of the field.

In searching for the cause of this effect, we found evidence in the literature that in cell culture media exposed to light from so-called sunlight lamps (with a high proportion of short-wave light), lethal photoproducts are formed. By the irradiation of tryptophane or tryptophane/riboflavine-containing media with near UV (365 nm), a toxic quantity of $H_2O_2$ was produced (McCormick, J. P., Fischer, J. R., Pachlatko, J. P., and Eisenstark, Science, 191,468–469 (1976); and Wang, R. J. and Nixon, B. T. In Vitro 14, No. 8 19–22 (1978)).

Peroxide and oxygen radicals are of special interest today with regard to senescence processes of cells and cell damage via toxic influences (e.g. as a result of hypoxia).

The following study investigated the influence of the active substance on this cell-damaging effect after exposure to the radiation from a halogen lamp.

The duration of the exposure which leads to a clear reduction of the survival of the cells but is not yet completely lethal was first determined in a preliminary experiment.

Method

Neurons from the hippocampus of rat embryos (day 17) were prepared as described previously. After 3 to 4 hours of growth in the incubator, the culture dishes were taken out and exposed to light. Afterwards fresh culture medium was added to the cultures in 3 concentration steps and these were then cultured for a further 20 hours. The survival of the cells was determined with the described fluorescence test. The controls were both illuminated and non-illuminated cells which were given fresh medium without the active substance at the same time.

Exposure

500 W halogen lamps with reflector, distance 40 cm (light value measured at the level of the Petri dishes: 18.5), 20 min exposure duration. During the exposure period, the culture dishes were placed in a temperature-controlled water bath. The temperature, which was measured directly in the medium, did not increase above 34° C.

Result

Figure 4:
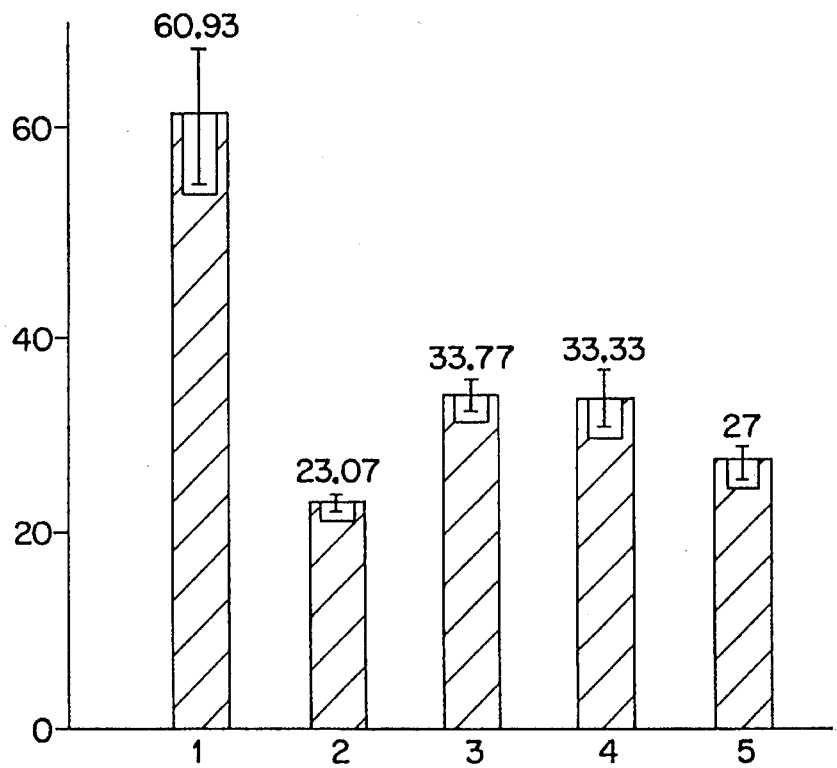
FIG. 4: A bar graph showing the LDH activity in rat cortex cultures lacking in glucose.
Figure 5:
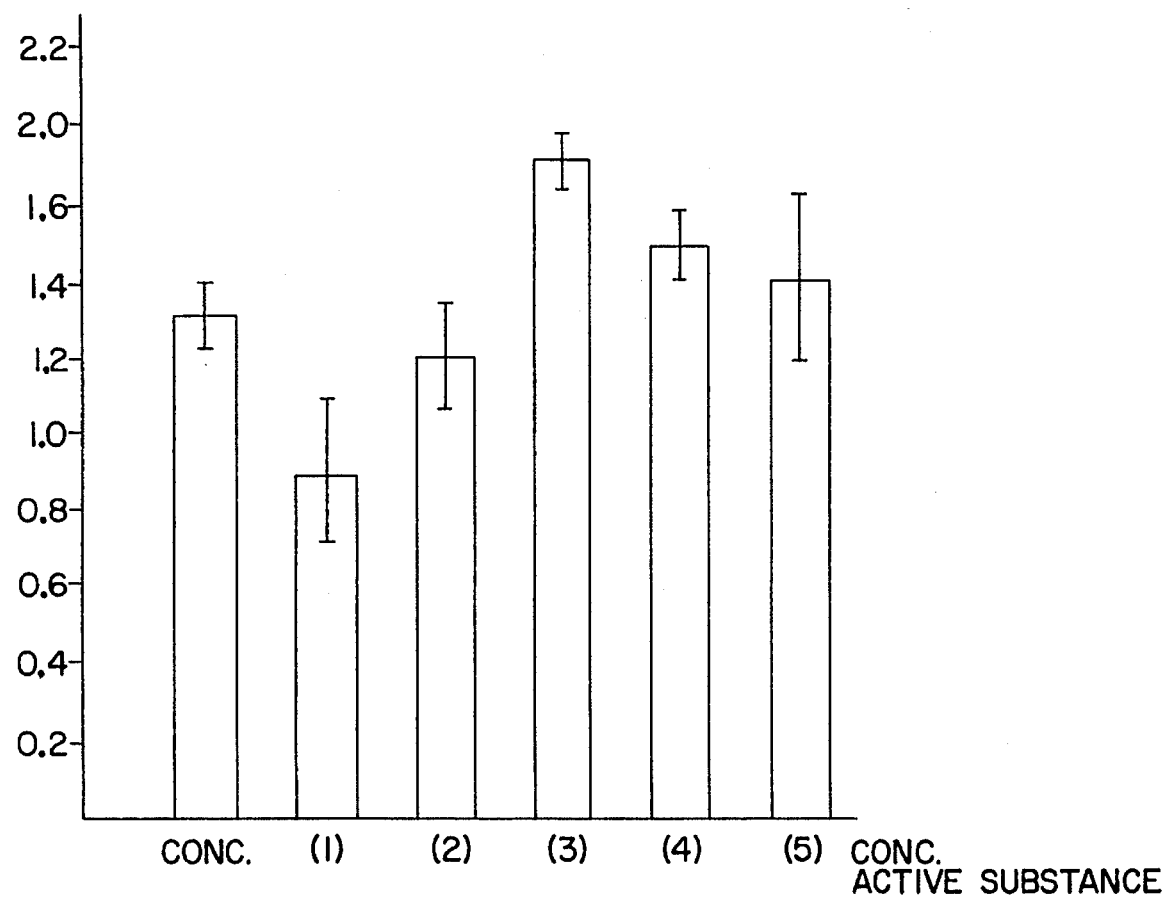
FIG. 5: A bar graph showing a vitality test with hippocampus neurons after 48 hours in vitro. The bars show the proportion of living/dead cells.

The result is shown in FIG. 4 which presents the percentage (SURVIVAL) of living cells after 24 hours in the culture.

1) Survival without exposure after 24 hours
2) After exposure without active substance
3) After exposure and after addition of 1 µg/ml active substance
4) After exposure and after addition of 0.1 µg/ml active substance
5) After exposure and after addition of 0.01 µg/ml active substance A clear effect on survival of the neurons in the cultures is seen under the described conditions. It is also noticeable here that a concentration (1µ g/ml) is effective which showed no positive survival effect after 48 hours under optimal conditions (see report I). It is possible that under normal conditions, a mildly toxic effect overlies the protective effect which predominates under light-caused damage conditions.

The question of which portion of the spectrum is most effective for the lethal effects was not examined. The possibility was ruled out, however, that the medium was heated up through the high proportion of long-wave radiation in the light and that the cells were damaged for this reason.

What is claimed is:

1. A virus-inhibiting composition, which is produced by a process comprising:
   (a) isolating a lignin unit containing fraction from a natural lignin containing material by extraction in an aqueous media under weakly acidic or alkaline conditions and separating the resultant insoluble solids;
   (b) isolating a lignoid unit containing fraction from a lignin containing product selected from the group consisting of wood-incarbonization products, bioconverted lignin containing material and mixtures thereof, by carrying out an aqueous alkaline extraction at a pH of 8 to 14 and separating the resultant alkali-insoluble solids; and
   (c) preparing a water-soluble polymer by reacting the lignin unit containing fraction from step (a) with the lignoid unit containing fraction from step (b), under aqueous alkaline conditions at a pH of about 9 to 12, removing by ultrafiltration a low molecular weight fraction having a molecular weight of, no more than 3000 daltons, isolating a fraction containing at least one polymer comprising lignin and having a molecular weight of 15 to 40 kilodaltons, discarding the resultant residue, and treating the 15 to 40 kildalton fraction with an hydrogen ion cation exchanger at a pH of 3 to 7.

2. The virus-inhibiting composition of claim 1, wherein the lignin containing fraction of step (a) is further processed to have a molecular weight less than 100 kD by adjusting the pH value to about 5 to 7 after extraction in the aqueous media and separating off the insoluble solids, subjecting the extraction solution to a molecular filtration which isolates a fraction having a molecular weight of less than 100 kD, discarding the resultant residue containing material having a molecular weight greater than 100 kD and directing said fraction having a molecular weight of less than 100 kD to step (c).

3. The virus-inhibiting composition of claim 1, wherein the lignoid unit containing fraction of step (b) is further processed to have a molecular weight of less than 40 kD by fragmenting the lignoid units in an alkaline solution, isolating a 15 to 35 kD containing fraction via molecular ultrafiltration and directing the 15 to 35 kD lignoid containing fraction to step (c).

4. The virus-inhibiting composition of claim 1, wherein a separation of the solids is carried out after the lignin unit containing fraction is reacted with the lignoid units containing fraction.

5. The virus-inhibiting composition of claim 1, wherein further processing of the 15 to 40 kilodalton fraction obtained from step (c) is carried out by means of particle filtering, pyrogen removal via filtering, and then sterilization.

6. The virus-inhibiting composition of claim 1, wherein the natural lignin containing material is selected from the group consisting of native wood, woody substances biotechnologically produced by the growing of plant-cell cultures, synthetic wood analogs obtained via the production of Freudenberg dehydration polymers from mono- and/or dilignoles and grafting the dehydration polymers on polysaccharide, lignin-polysaccharide complexes obtained by alkaline extraction from chlorite wood cellulose, and mixtures thereof.

7. The virus-inhibiting composition of claim 1, wherein the lignin containing product in step (b) is selected from the group consisting of wood bioconverted by lignolytically active micro-organisms, wood bioconverted through the effect of isolated lignolytic enzymes, and mixtures thereof.

8. The virus-inhibiting composition of claim 1, wherein an alkali is used in step (a), step (b) or both steps (a) and (b), and the alkali is selected from the group consisting of KOH, NaOH, LiOH and ammonia.

9. The virus-inhibiting composition of claim 1, wherein the lignin unit containing fraction in step (a) is in a concentration of 0.05 to 10% by weight.

10. The virus-inhibiting composition of claim 1, wherein the extraction in step (a) is carried out at a pH value of 12 to 14.

11. The virus-inhibiting composition of claim 1, wherein the extraction in step (a) is carried out at a temperature between 100° C. and 120° C., in an autoclave.

12. The virus inhibiting composition of claim 1, wherein the lignin containing product in step (b) comprise wood incarbonization products selected from the group consisting of lignites and colored coals.

13. The virus inhibiting composition of claim 1, wherein the alkaline extraction in step (b) is carried out with 0.1 to 0.8 M KOH at room temperature.

14. The virus-inhibiting composition of claim 3, wherein the fragmenting is carried out over 7 to 10 days at a pH of 11 with KOH at room temperature.

15. The virus-inhibiting composition of claim 1, wherein the preparation of the water-soluble polymer in step (c) occurs at a temperature between room temperature and 120° C.

16. The virus-inhibiting composition of claim 1, wherein the fraction containing at least one polymer in step (c) has a molecular weight between 18 and 38 kD.

17. The virus-inhibiting composition of claim 1, wherein the treatment with the hydrogen ion cation exchanger in step (c) is carried out until reaching a stable pH value of 4 to 6.8.

18. The virus-inhibiting composition of claim 1, which further comprises removing pyrogens from the water-soluble polymer from step (c) by filtering.

19. The virus-inhibiting composition of claim 1, wherein the lignolytic enzyme is phenoloxidase.

20. The virus-inhibiting composition of claim 9, wherein the lignin unit containing a fraction in step (a) is in a concentration of up to about 2% by weight.

21. The virus-inhibiting a composition of claim 9, wherein the lignin unit containing fraction in step (a) is in a concentration of about 1% by weight.

22. The virus-inhibiting composition of claim 10, wherein the extraction is carried out with KOH for 1 to 10 days at 20° C.

23. The virus-inhibiting composition of claim 13, wherein the alkaline extraction is carried out with 0.4M KOH.

24. The virus-inhibiting composition of claim 15, wherein in step (c), the pH value during the reaction is between 10 to 12.

25. The virus-inhibiting composition of claim 17, wherein in step (c), the treating with the cation exchanger is carried out until the pH is 5 to 6.

26. The virus-inhibiting composition of claim 18, which further comprises carrying out sterilization after said filtering, said sterilization being carried out by autoclaving at 121° C. for over 14 minutes.

27. The virus-inhibiting composition of claim 1, wherein step (a) is carried out by extracting a wood selected from the group consisting of Siberian larch heartwood and European beechwood at a temperature of 46° to 66° C. at a pH of 11.5; and step (b) is carried out at a pH of 5.5 by extracting brown coal or lignite.

28. The virus-inhibiting composition of claim 1, wherein the composition is in the form of a chelate of a noble metal selected from the group consisting of Pt, Au and Pd.

29. A pharmaceutical composition for parenteral or local administration comprising a therapeutically effective amount of the virus-inhibiting composition of claim 1 in combination with a pharmaceutically acceptable carrier.

* * * * *